United States Patent [19]

Arnold et al.

[11] Patent Number: 4,900,404

[45] Date of Patent: Feb. 13, 1990

[54] PHOSPHATE SELECTIVE MEMBRANE ELECTRODE

[75] Inventors: Mark A. Arnold, Coralville; Scott A. Glazier, Iowa City, both of Iowa

[73] Assignee: University of Iowa Research Foundation, Iowa City, Iowa

[21] Appl. No.: 232,006

[22] Filed: Aug. 15, 1988

[51] Int. Cl.$^4$ ............................................. G01N 27/30
[52] U.S. Cl. ..................................... 204/1 T; 204/418
[58] Field of Search ................................ 204/1 T, 418

[56] References Cited

U.S. PATENT DOCUMENTS 3,445,365  5/1969  Ross ................................... 204/417
4,735,692  4/1988  Arnold et al. ..................... 204/1 T

OTHER PUBLICATIONS

Zarinski, V. A. et al., "Electrochemical Properties of Liquid Membranes on Dialkyltin (IV) Compounds in Phosphorous (V) Solutions", UDC 543.257.5:546.18, V.I. Vernadskii Institute of Geochemistry and Analytical Chemistry, Acad. of Sci. of the USSR, Moscow, translated from Zhurnal Analiticheskoi Khimii, vol. 35, No. 11.

Zarinski V. A., et al. "Dialkyltin(IV) Compounds as Active Components of the Liquid Membranes of Ion-Selective Electrodes in Arsenic(V) Solutions", UDC 543.257.1:546.19, V.I. Vernadskii Institute of Geochemistry and Analytical Chem. Academy of Sciences of the USSR, Moscow, translated from Zhurnal Analiticheskoi Khimii, vol. 35, No. 11, pp. 2143-2148, Nov. 1980.

Primary Examiner—John F. Niebling
Assistant Examiner—David G. Ryser
Attorney, Agent, or Firm—Henderson & Sturm

[57] ABSTRACT

An improved phosphate selective membrane electrode using bis(p-chlorobenzyl)tin dichloride as the membrane active component. In addition to this tin compound, the membrane contains N,N-dimethylformamide (DMF), a strong complexing agent for tin compounds.

12 Claims, 2 Drawing Sheets

4,900,404

PHOSPHATE SELECTIVE MEMBRANE ELECTRODE

TECHNICAL FIELD

This invention relates to an ion-selective membrane electrode, and more particularly to an ion-selective electrode with improved response and selectivity characteristics for phosphate anions.

BACKGROUND ART

Phosphate ion is an extremely important species in many fields. Phosphate is present in numerous biological systems, is a major constituent of many minerals and fertilizers, and is a component of industrial wastewater. Phosphate is an important analyte, yet only one basic method exists for its assay.

The importance of orthophosphate concentration levels spans all areas of science and technology. A system that can continuously and selectively monitor phosphate levels in aqueous solutions will find numerous applications in fields such as pharmacology, biomedical research, clinical chemistry, industrial process monitoring, environmental monitoring, etc. Past attempts to develop a selective membrane electrode for phosphate have not been successful. Much of this past work has involved construction of electrodes based on membranes composed of various insoluble salts. In general, electrodes with either poor selectivity over common anions or impractically high detection limits have resulted from these previous attempts. A variety of liquid membranes and systems based on enzymatic reactions have also been investigated and found to be unsuitable for the selective determination of orthophosphate.

A series of extracting agents for phosphate and arsenate anions have been introduced. Long chain dialkyltin dinitrate species, such as dioctyltin dinitrate and didodecyltin dinitrate, are used to separate phosphate and arsenate from other anions by selective extraction into an organic layer. Liquid membrane electrodes employing these extraction agents have been demonstrated. Although it has been unsuccessful in developing phosphate selective polymer membrane electrodes with dialkyltin salts, it has been discovered that the incorporation of dibenzyltin dichloride derivatives into a plasticized PVC membrane gives a selective response to phosphate. Resulting electrodes possess practical detection limits and useful dynamic ranges of response.

Membrane electrodes containing dibenzyltin dichloride or bis(p-methylbenzyl)tin dichloride as active material have been disclosed in U.S. Pat. No. 4,735,692 which is incorporated herein by reference. Subsequent studies have shown that the response and selectivity characteristics of this known electrode were lacking in many respects.

Those concerned with these and other problems recognize the need for an improved phosphate selective membrane electrode.

DISCLOSURE OF THE INVENTION

The present invention provides an improved phosphate selective membrane electrode using bis(p-chlorobenzyl)tin dichloride as the membrane active component. In addition to this tin compound, the membrane contains N,N-dimethylformamide (DMF), a strong complexing agent for tin compounds.

The exact role DMF takes in establishing electrode response is not known at this time. Simon and co-workers (Mikrochimica Acta [Wien] 1986 III, 225), in studies on triorganotin compounds as active materials for membrane electrodes, have added compounds to their membranes which may play a role similar to DMF in determining electrode response and selectivity. DMF and other complexing agents like DMF are thought to be important additives for the membrane.

The previously disclosed membrane electrodes containing dibenzyltin dichloride or bis(p-methylbenzyl)tin dichloride as active material have been found to be inferior in many respects to the present electrodes containing bis(p-chlorobenzyl)tin dichloride as active material (with DMF as an additive). The present electrode has been studied much more extensively than the previously disclosed electrodes. The results of these studies clearly show the superior selectivity of the bis(p-chlorobenzyl)tin dichloride containing electrode for phosphate over many common anions. In addition to enhanced selectivity, the limit of detection and linear response range for phosphate are improved. None of the other electrodes constructed in the past employing organotin compounds have proven to be very responsive or selective for orthophosphate.

An object of the present invention is the provision of an improved phosphate selective membrane electrode using bis(p-chlorobenzyl)tin dichloride as the membrane component.

Another object of the present invention is to provide a phosphate selective membrane electrode that shows superior selectivity for phosphate over many common anions.

A further object of the invention is the provision of an improved limit of detection and linear response for phosphate.

Still another object is to provide an electrode that employs bis(p-chlorobenzyl)tin dichloride as a membrane active component.

A still further object of the present invention is the provision of an electrode employing organotin compounds that have proven to be responsive and selective for orthophosphate.

Yet another object of the present invention is the provision of an electrode that possesses greater selectivity for phosphate over ions such as chloride, nitrate, bromide, iodide, sulfate, and acetate.

BRIEF DESCRIPTION OF THE DRAWINGS

These and other attributes of the invention will become more clear upon a thorough study of the following description of the best mode for carrying out the invention, particularly when reviewed in conjunction with the drawings, wherein.

BEST MODE FOR CARRYING OUT THE INVENTION

Figure 1:
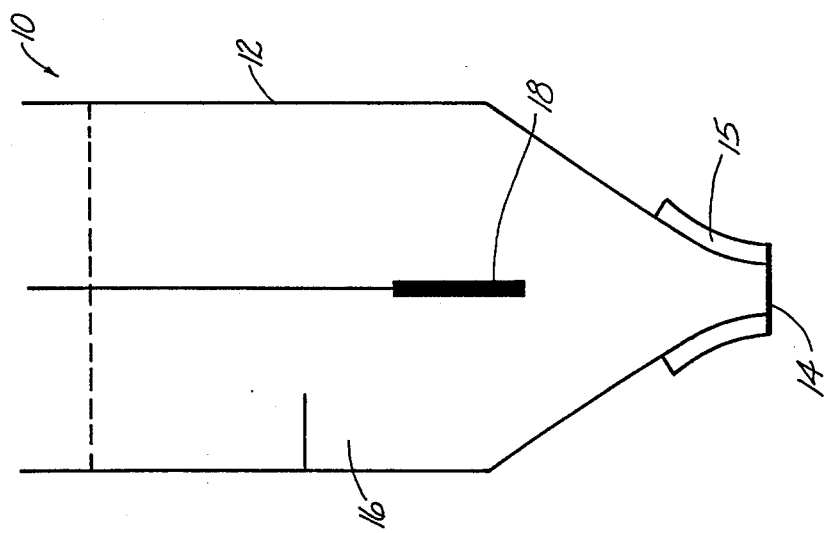
FIG. 1 is a schematic representation of the disclosed phosphate selective electrode.

Referring now to the drawings, wherein like reference numerals designate identical or corresponding parts throughout the several views, FIG. 1 shows the phosphate selective membrane electode generally designated by the reference numeral 10. The electrode (10) includes a body section (12) formed of a disposable pipet tip and having a lower opening sealed by a phosphate selective polymer membrane (14). The body section (12) contains an internal reference solution (16) of 0.1M KCl and an internal reference electrode (18) comprising a Ag/AgCl reference wire. The phosphate selective membrane (14) owes its sensitivity to a di-substituted aryl tin compound used as a membrane active component.

Composition of the selective membrane (14) includes bis(p-chlorobenzyl)tin dichloride together with N,N-dimethylformamide in a poly(vinyl chloride) (PVC) matrix. The resulting electrode (10) demonstrates selectivity for orthophosphate over many common anions, such as sulfate, acetate, chloride, bromide, nitrate and iodide. A detection limit of $3.4 \times 10^{-5}$ M and a linear range of response from $2.2 \times 10^{-4}$ M to $1.2 \times 10^{-2}$ M are obtained when operated in a pH 7.0 buffer. Slopes of $-32.9 \pm 0.3$ mV/decade are obtained which match the theoretical value of the dibasic species. In addition, the electrode lifetime is at least 28 days when electrodes are stored in this buffer at room temperature. When stored dry, the membranes are stable for at least one month.

Orthophosphate selective electrodes (10) were constructed by formation of the active PVC membrane (14) at the tip of a short length of Nalgene tubing (15). The polymer membrane was formed by dipping the electrode tip in a membrane casting solution and allowing the solvent of this solution to evaporate between successive applications. The membrane casting solution consisted of 70.5 mg bis(p-chlorobenzyl)tin dichloride, 133.5 mg PVC (High molecular weight; Aldrich Chemical Co., Milwaukee, Wis.), 141.9 mg dibutyl sebacate (Eastman Kodak Co., Rochester, N.Y.), 48.3 mg N,N-dimethylformamide (Omnisolve; EM Science, Cherry Hill, N.J.), and 3 mL tetrahydrofuran (Gold Label; Aldrich Chemical Co.). Bis(p-chlorobenzyl)tin dichloride was synthesized according to the procedure of Kinugawa et al.

Electrode response was obtained in a pH $7.00 \pm 0.01$ working buffer that consisted of 10 mM tris(hydroxymethyl) aminomethane (Tris) with a 4.5 mM sulfuric acid. All interference studies were carried out in this buffer and the pH was continuously monitored and maintained at $7.00 \pm 0.01$ throughout. Electrodes were conditioned prior to operation by soaking the polymer membrane in 1 liter of the working buffer for 20 hours followed by a brief exposure to 10 mM phosphate. Ion activities were calculated based on the theory of Davies.

The response to dibasic orthophosphate for a series of anion-responsive membrane electrodes is discussed below for electrodes prepared with (1) a conventional tetraalkylammonium ion-exchanger ($R_4N^+$), (2) bis(p-methylbenzyl)tin dichloride, (3) dibenzyltin dichloride, and (4) bis(p-chlorobenzyl)tin dichloride. Each response represents the average of eight individual electrodes.

The tetraalkylammonium ion-exchanger membrane yields minimal response to orthophosphate as expected. The response for conventional membranes, such as this, is based on a combination of simple ion-exchange and ion lipophilicity. Increase in the lipophilicty of the anion makes it easier for it to enter the lipophilic membrane and, therefore, to generate a response. As a result, conventional anion selective electrodes respond well to lipophilic anions (such as thiocyanate), but they respond poorly to oxy-anions (such as orthophosphate).

In contrast, membranes based on the tin compounds all respond better to orthophosphate than the tetraalkylammonium ion based membranes. Within the group of tin compounds, the bis(p-chloro) derivative provides the best response toward orthophosphate. The bis(p-chloro) derivative provides the best response toward orthophosphate. The bis(p-chloro) derivative provides a linear response to dibasic orthophosphate from 0.2 to 12.9 mM with a slope of $-33.0 \pm 0.1$ mV/decade. This slope closely matches the theoretical Nernstian value of $-29.6$ mV/decade for a divalent anion. Detection limit for this membrane electrode is $0.034 \pm 0.002$ mM. In comparison, detection limits of $0.249 \pm 0.008$ and $0.134 \pm 0.007$ mM have been measured for the bis(p-methylvenzyl) tin dichloride and dibenzyltin dichloride based membranes, respectively. An enhancement in the detection limit of approximately one order of magnitude is achieved with the bis(p-choro) derivative. The response from the tetraalkylammonium ion based membrane is so poor for orthophosphate that a detection limit cannot be accurately estimated from its response curve.

Figure 2:
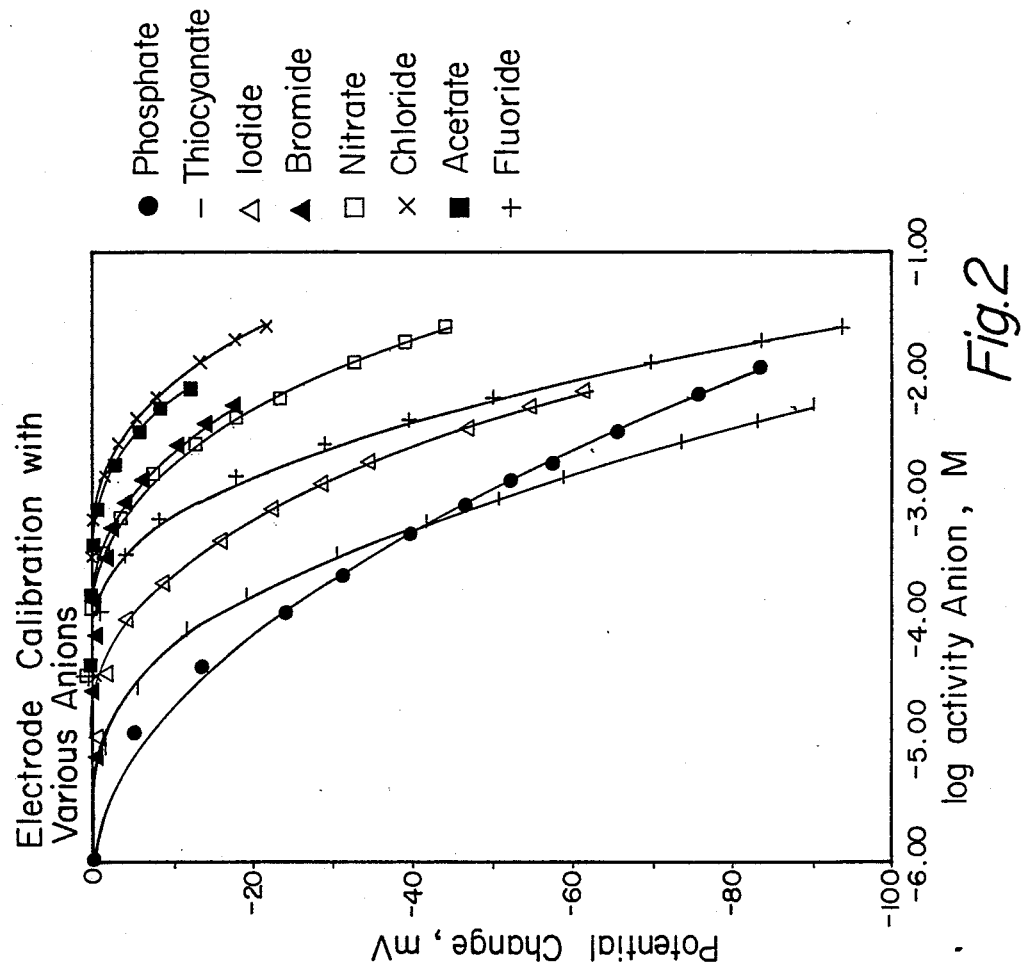
FIG. 2 is a graph showing the response performance of the electrode of the present invention to various anions using a buffer of 0.01M Tris-H$_2$SO$_4$, pH 7.00 using potassium salts of the anions.

Electrode selectivity has been measured by directly comparing the electrode response to orthophosphate and to other common anions. FIG. 2 shows the response from electrodes composed of the bis(p-chloro) derivative to orthophosphate, thiocyanate, iodide, fluoride, nitrate, bromide, chloride, and acetate.

Electrode selectivity has been quantified by using activity ratios. These activity ratios indicate the apparent phosphate activity (concentration) for a given activity of the interfering ion (apparent orthophosphate activity/corresponding interfering ion activity). Values greater than unity indicate the electrode is more selective for the interfering ion, values less than unity indicate the electrode is more selective for orthophosphate, and a value of unity indicates equal selectivity for the two ions in quesetion. Absolute specificity is indicated by an activity ratio of zero.

Table 1 lists the activity ratios for orthophosphate over the anions tested. Values are represented for each of the membranes studied (tetraalkylammonium ion, bis(p-methylbenzyl) tin dichloride, dibenzyltin dichloride, and bis(p-chlorobenzyl)tin dichloride). All of the tin-based membranes display greater selectivity for orthophosphate than the conventional membrane. In addition, selectivity for orthophosphate increases in going from the bis(p-methyl) to the dibenzyl to the bis(p-chloro) derivatives. Values above zero of the logarithm of the activity ratio for each of the membranes examined and for each of the anions tested demonstrate selectivity for the interfering ion and those less than zero indicate selectivity for phosphate. An improvement in selectivity of more than three orders of magnitude is provided by the bis(p-chloro) derivative in comparison to conventional anion selective membrane electrodes.

As expected, slopes of the response curves for these anions differ according to the magnitude of charge on the anion tested (see FIG. 2). A slope of $-59.16$ mV/decade is expected for monovalent anions, while a slope of only $-29.58$ mV/decade is expected for divalent anions. Differences in response slope result in a concentration dependency for the activity ratios and the electrode selectivity. Such concentration dependent selectivity must be considered in the methodology development stage.

Overall, the selectivity pattern for the bis(p-chloro) derivative is:

$HPO_4^= \approx SCN^- > I^- > F^- > NO_3^- > Br^- > Cl^- \approx OAc^-$

TABLE 1

Activity Ratios* for Tested Anion-Responsive Membrane Electrodes.

|  | $R_4N^+$ | bis-(p-Methyl) | Dibenzyl | bis(p-Chloro) |
|---|---|---|---|---|
| thiocyanate ($SCN^-$) | 446 | 135 | 23 | 0.87 |
| iodide ($I^-$) | 310 | 24 | 8.7 | 0.17 |
| fluoride ($F^-$) | — | — | — | 0.13 |
| nitrate ($NO_3^-$) | 62 | 3.6 | 0.76 | 0.014 |
| bromide ($Br^-$) | 24 | 1.8 | 0.52 | 0.0087 |
| chloride ($Cl^-$) | 1.1 | 0.35 | 0.11 | 0.0026 |
| acetate ($OAc^-$) | — | — | — | 0.0033 |

*Apparent Dibasic Orthophosphate Conc/Interferent Conc

Usable calibration curves for dibasic orthophosphate are obtained over a 28 day period when electrodes are stored in the working buffer at room temperature between measurements. After approximately two weeks of use, however, the detection limit begins to gradually deteriorate and slightly shorter linear ranges are observed. Detection limits below the millimolar activity level are observed even after 28 days. Prepared membranes that are kept dry (under conditions of ambient humidity) at room temperature can be stored for at least one month without any detectable adverse effect on electrode calibration or selectivity.

The dis(p-chlorobenzyl)tin dichloride based membrane electrode possesses selectivity for dibasic orthophosphate that is clearly superior to previous anion-selective polymer membrane electrodes. Based on the excellent selectivity, low detection limits and favorable lifetimes of this membrane electrode, development of practical continuous monitor systems for orthophosphate is now possible.

While only certain preferred embodiments of this invention have been shown and described by way of illustration, many modifications will occur to those skilled in the art and it is, therefore, desired that it be understood that it is intended herein to cover all such modifications that fall within the true spirit and scope of this invention.

We claim:

1. A phosphate ion selective membrane electrode comprising:
a body member having an opening therein;
a membrane sealably attached to said body member over said opening, said membrane including
a disubstituted aryl tin compound, and
a strong complexing agent for tin compounds;
a reference solution contained within said body member; and
a reference electrode disposed within said body member in contact with said reference solution.

2. The electrode of claim 1 wherein said disubstituted aryl tin compound is selected from a group consisting of dibenzyltin dichloride and derivatives thereof.

3. The electrode of claim 2 wherein said disubstituted aryl tin compound is bis(p-chlorobenzyl)tin dichloride.

4. The electrode of claim 3 wherein said strong complexing agent for tin compounds is N,N-dimethylformamide.

5. The electrode of claim 2 wherein said strong complexing agent for tin compounds is N,N-dimethylformamide.

6. The electrode of claim 1 wherein said strong complexing agent for tin compounds is N,N-dimethylformamide.

7. A method of determining the phosphate anion in a sample including the step of:
contacting said sample with an electrode comprising:
a body member having an opening therein;
a membrane sealably attached to said body member over said opening, said membrane including
a disubstituted aryl tin compound, and;
a strong complexing agent for tin compounds;
a reference solution contained within said body member; and
a reference electrode disposed within said body member in contact with said reference solution.

8. The method of claim 7 wherein said disubstituted aryl tin compound is selected from a group consisting of dibenzyltin dichloride and derivatives thereof.

9. The method of claim 8 wherein said disubstituted aryl tin compound is bis(p-chlorobenzyl)tin dichloride.

10. The method of claim 9 wherein said strong complexing agent for tin compounds is N,N-dimethylformamide.

11. The method of claim 8 wherein said strong complexing agent for tin compounds is N,N-dimethylformamide.

12. The method of claim 7 wherein said strong complexing agent for tin compounds is N,N-dimethylformamide.

* * * * *